US00PP34115P2

(12) United States Plant Patent
Hofmann

(10) Patent No.: US PP34,115 P2
(45) Date of Patent: Apr. 5, 2022

(54) ***JAMESBRITTENIA* PLANT NAMED 'INJAMSADAW'**

(50) Latin Name: *Jamesbrittenia hybrida*
Varietal Denomination: INJAMSADAW

(71) Applicant: Silvia Hofmann, Mainz (DE)

(72) Inventor: Silvia Hofmann, Mainz (DE)

(73) Assignee: INNOVAPLANT ZIERPFLANZEN GmbH & Co., Gensingen (DE)

( * ) Notice: Subject to any disclaimer, the term of this patent is extended or adjusted under 35 U.S.C. 154(b) by 0 days.

(21) Appl. No.: 17/372,138

(22) Filed: Jul. 9, 2021

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./263.1, 485
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct *Jamesbrittenia* plant named 'INJAMSADAW', characterized by its compact, upright to outwardly spreading and mounding to trailing and decumbent plant habit; vigorous growth habit and rapid growth rate; freely branching habit; dense and bushy plant form; early and freely flowering habit; single-type flowers that are purple and bright yellow in color; relative resistance to *Botrytis*; and excellent garden performance.

2 Drawing Sheets

Figure 1:
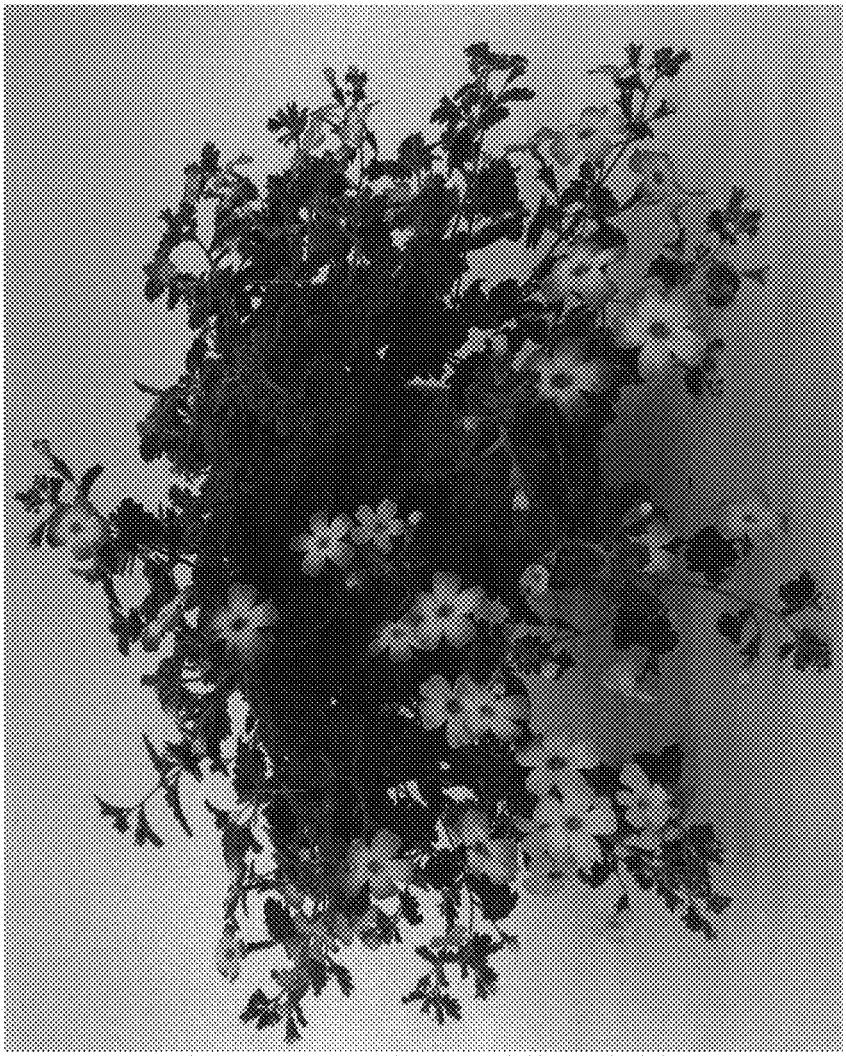

Botanical designation: *Jamesbrittenia hybrida.*
Cultivar denomination: 'INJAMSADAW'.

CROSS-REFERENCED TO CLOSELY-RELATED APPLICATIONS

Title: *Jamesbrittenia* Plant Named 'INJAMSASKY'
Inventor/Applicant: Silvia Hofmann
application Ser. No. 17/372,166
Filed: Concurrently with the instant application

BACKGROUND OF THE INVENTION

The present invention relates to a new and distinct cultivar of *Jamesbrittenia* plant, botanically known as *Jamesbrittenia hybrida*, commonly referred to as South African Phlox and hereinafter referred to by the name 'INJAMSADAW'.

The new *Jamesbrittenia* plant is a product of a planned breeding program conducted by the Inventor in Heidesheim and Gensingen, Germany. The objective of the breeding program is to create new compact, freely-branching and uniformly mounding *Jamesbrittenia* plants with early and freely flowering habit, attractive flowers and good garden performance.

The new *Jamesbrittenia* plant originated from a cross-pollination made by the Inventor in August, 2017 in Heidesheim, Germany of *Jamesbrittenia hybrida* 'Shakira Yellow', not patented, as the female, or seed, parent with a proprietary selection of *Jamesbrittenia hybrida* identified as code number Ja 16 15-6, not patented, as the male, or pollen, parent. The new *Jamesbrittenia* plant was discovered and selected by the Inventor as a single flowering plant within the progeny of the stated cross-pollination in a controlled greenhouse environment in Heidesheim, Germany in July, 2018.

Asexual reproduction of the new *Jamesbrittenia* plant by vegetative terminal cuttings in a controlled greenhouse environment in Gensingen, Germany since July, 2018 has shown that the unique features of this new *Jamesbrittenia* plant are stable and reproduced true to type in successive generations.

SUMMARY OF THE INVENTION

Plants of the new *Jamesbrittenia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INJAMSADAW'. These characteristics in combination distinguish 'INJAMSADAW' as a new and distinct *Jamesbrittenia* plant:

1. Compact, upright to outwardly spreading and mounding to trailing and decumbent plant habit.
2. Vigorous growth habit and rapid growth rate.
3. Freely branching habit; dense and bushy plant form.
4. Early and freely flowering habit.
5. Single-type flowers that are purple and bright yellow in color.
6. Relative resistance to *Botrytis.*
7. Excellent garden performance.

Plants of the new *Jamesbrittenia* can be compared to plants of the female parent, 'Shakira Yellow'. In side-by-side comparisons, plants of the new *Jamesbrittenia* differ primarily from plants of 'Shakira Yellow' in flower color as plants of the new *Jamesbrittenia* have purple and bright yellow-colored flowers whereas plants of 'Shakira Yellow' have bright yellow-colored flowers.

Plants of the new *Jamesbrittenia* can be compared to plants of the male parent selection. In side-by-side comparisons, plants of the new *Jamesbrittenia* differ primarily from plants of the male parent selection in flower color as plants of the new *Jamesbrittenia* have purple and bright yellow-colored flowers whereas plants of the male parent selection have red-colored flowers.

Plants of the new *Jamesbrittenia* can be compared to plants of *Jamesbrittenia hybrida* 'INJAMSASKY', disclosed in a U.S. Plant Patent filed concurrently. In side-by-side comparisons, plants of the new *Jamesbrittenia* differ primarily from plants of 'INJAMSASKY' in flower color as plants of the new *Jamesbrittenia* have purple and bright yellow-colored flowers whereas plants of 'INJAMSASKY' have light reddish purple and white-colored flowers.

Plants of the new *Jamesbrittenia* can also be compared to plants of *Jamesbrittenia hybrida* 'Goldstar', not patented. In side-by-side comparisons, plants of the new *Jamesbrittenia* differ primarily from plants of 'Goldstar' in the following characteristics:

1. Plants of the new *Jamesbrittenia* are more vigorous than plants of 'Goldstar'.
2. Plants of the new *Jamesbrittenia* are more freely branching than plants of 'Goldstar'.
3. Plants of the new *Jamesbrittenia* have a stronger root system than plants of 'Goldstar'.
4. Plants of the new *Jamesbrittenia* have purple and bright yellow-colored flowers whereas plants of 'Goldstar' have yellow-colored flowers.

BRIEF DESCRIPTION OF THE PHOTOGRAPHS

The accompanying colored photographs illustrate the overall appearance of the new *Jamesbrittenia* plant showing the colors as true as it is reasonably possible to obtain in colored reproductions of this type. Colors in the photographs may differ slightly from the color values cited in the detailed botanical description which accurately describe the colors of the new *Jamesbrittenia* plant.

The photograph on the first sheet (FIG. 1) is a side perspective view of a typical flowering plant of 'INJAMSADAW' grown in a container.

Figure 2:
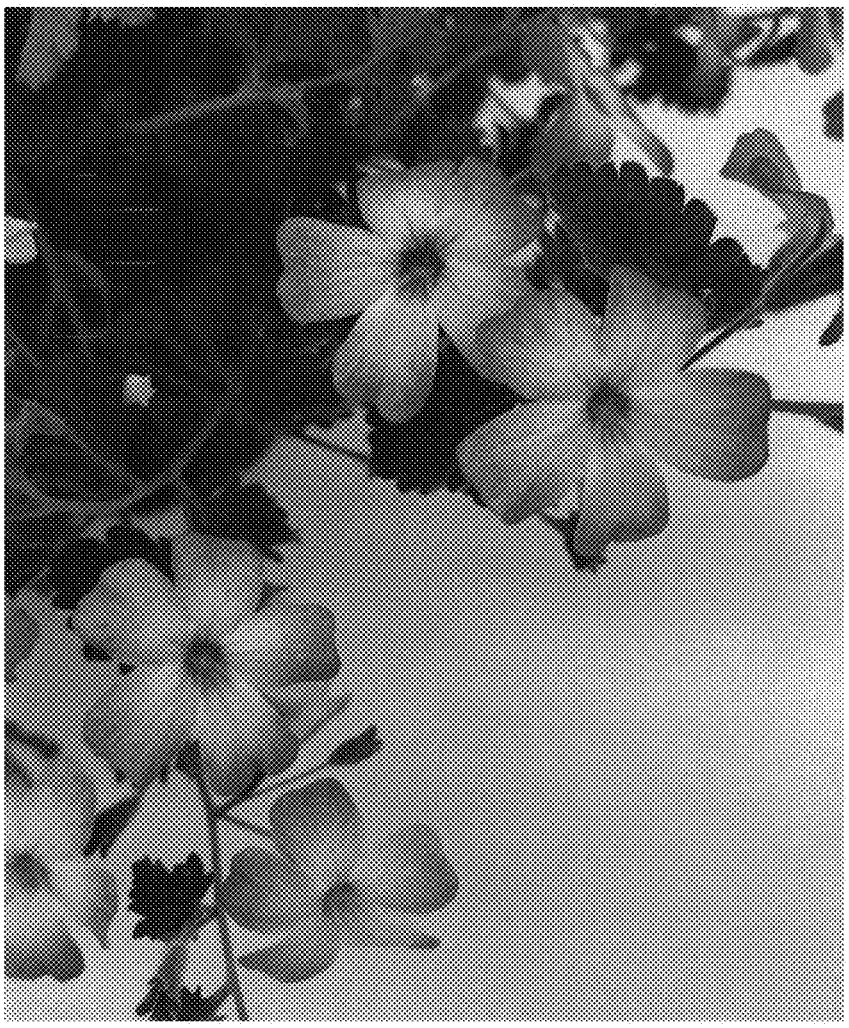

The photograph on the second sheet (FIG. 2) is a close-up view of a typical flowering plant of 'INJAMSADAW'.

DETAILED BOTANICAL DESCRIPTION

The aforementioned photographs and following observations and measurements describe plants grown during the autumn and winter in 10.8-cm containers in a glass-covered greenhouse in Loudon, New Hampshire and under cultural practices typical of commercial *Jamesbrittenia* production. During the production of the plants, average daily temperatures were 18° C. Plants were grown under long day/short night conditions and were pinched two weeks after planting. Plants were ten weeks from planting when the photographs and description were taken. In the following description, color references are made to The Royal Horticultural Society Colour Chart, 2015 Edition, except where general terms of ordinary dictionary significance are used. Measurements were taken on individual plants.

Botanical classification: *Jamesbrittenia hybrida* 'INJAMSADAW'.

Parentage:

*Female, or seed, parent.*—*Jamesbrittenia hybrida* 'Shakira Yellow', not patented.

*Male, or pollen, parent.*—Proprietary selection of *Jamesbrittenia hybrida* identified as code number Ja 16 15-6, not patented.

Propagation:

*Type.*—Terminal vegetative cuttings.

*Time to initiate roots, summer.*—About five to seven days at temperatures about 21° C. to 27° C.

*Time to initiate roots, winter.*—About seven to ten days at temperatures about 18° C. to 21° C.

*Time to produce a rooted young plant, summer.*—About three to four weeks at temperatures about 21° C. to 27° C.

*Time to produce a rooted young plant, winter.*—About four to five weeks at temperatures about 16° C. to 18° C.

*Root description.*—Fine, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Compact, upright to outwardly spreading and mounding to trailing and decumbent plant habit; freely branching habit with lateral branches potentially developing at every node, dense and bushy plant form; pinching enhances development of lateral branches; vigorous growth habit and rapid growth rate.

*Plant height.*—About 7 cm to 9 cm.

*Plant diameter* (*area of spread*).—About 38 cm by 40 cm.

*Lateral branches.*—Length: About 23 cm. Diameter: About 2 mm. Internode length: About 2 cm to 2.5 cm. Strength: Strong; flexible, wiry. Aspect: Initially upright then outwardly spreading to trailing and decumbent. Texture and luster: Densely pubescent; moderately glossy. Color, developing and developed: Close to 144A.

Leaf description:

*Arrangement.*—Opposite; leaves simple.

*Length.*—About 3.25 cm.

*Width.*—About 3 cm.

*Shape.*—Ovate to deltoid.

*Apex.*—Bluntly acute.

*Base.*—Truncate with cuneate tendencies.

*Margin.*—Deeply crenate with shallow lobing; sinuses divergent.

*Texture and luster, upper surface.*—Moderately pubescent; slightly glossy.

*Texture and luster, lower surface.*—Mostly glabrous with pubescence along veins and margins; slightly glossy.

*Venation pattern.*—Pinnate.

*Color.*—Developing leaves, upper surface: More green than 146A. Developing leaves, lower surface: Close to 146B. Fully developed leaves, upper surface: More green than between 146A and 147A; venation, close to 146A. Fully developed leaves, lower surface: Close to 147B; venation, close to 146B to 146C.

*Petioles.*—Length: About 7 mm to 9 mm. Diameter: About 1 mm to 1.5 mm. Strength: Strong, flexible. Texture and luster, upper and lower surfaces: Pubescent; moderately glossy. Color, upper surface: Close to 147A. Color, lower surface: Close to 146A.

*Stipules*.—Quantity and arrangement: Two at petiole attachment to stein. Length: About 1.2 cm. Width: About 9 mm. Shape: Ovate to deltoid. Color, upper surface: More green than between 146A to 147A. Color, lower surface: Close to 146A.

Flower description:

*Flower type and flowering habit*.—Single terminal and axillary star-shaped salverform flowers; flowers face mostly upward to slightly outwardly; freely flowering habit with flowers potentially forming at every node.

*Natural flowering season*.—Long flowering period, plants flower from early spring until the autumn, flowering continuous during this period; early flowering habit.

*Flower longevity on the plant*.—About three to five days; persistent.

*Fragrance*.—None detected.

*Flower buds*.—Length: About 5 mm. Diameter: About 2.5 mm. Shape: Oblong. Texture and luster: Pubescent; moderately glossy. Color: Close to 144A.

*Flower diameter*.—About 2.25 cm to 2.5 cm.

*Flower depth* (*height*).—About 1.5 cm to 1.75 cm.

*Throat diameter*.—About 2.5 mm.

*Tube length*.—About 1.25 cm to 1.5 cm.

*Tube diameter, proximally*.—About 1 mm.

*Petals*.—Quantity and arrangement: Five petals fused in a single salverform whorl. Petal lobe length (from throat): About 1.1 cm to 1.25 cm. Petal lobe width: About 8 mm to 9 mm. Petal lobe shape: Spatulate. Petal lobe apex: Truncate and retuse. Petal lobe margin: Entire; not undulate. Petal lobe texture and luster, upper surface: Smooth, glabrous; velvety; slightly glossy. Petal lobe texture and luster, lower surface: Smooth, glabrous; slightly glossy. Throat texture and luster: Smooth, glabrous; slightly glossy. Tube texture and luster: Densely pubescent; matte. Color: When opening, upper surface: Distally, close to 9A overlain with close to N81A and proximally, close to 154D. When opening, lower surface: Close to 157D faintly overlain with close to N81A. Fully opened, upper surface: Distally, close to 9A overlain with close to N81A and proximally, close to 11A; venation, similar to lamina colors; colors becoming closer to N78A and 10A with subsequent development. Fully opened, lower surface: Close to 157D faintly overlain with close to N81A; venation, similar to lamina color; color does not change with subsequent development. Flower throat (inside): Distally, close to 17A and proximally, close to 13A; venation, similar to lamina colors. Flower tube (outside): Distally, close to 154D and proximally, close to N81A; venation, similar to lamina colors.

*Sepals*.—Quantity and arrangement: Five sepals fused in a single star-shaped whorl. Calyx length: About 1 cm. Calyx diameter: About 3 mm. Sepal length: About 1 cm. Sepal width: About 1.5 mm. Shape: Narrowly oblong. Apex: Bluntly acute; flared at the apex. Margin: Entire. Texture and luster, upper surface: Moderately pubescent; slightly to moderately glossy. Texture and luster, lower surface: Densely pubescent; slightly to moderately glossy. Color: When opening and fully developed, upper surface: Close to 144A. When opening and fully developed, lower surface: Close to 144A.

*Peduncles*.—Length: About 1 cm to 1.25 cm. Width: About 1 mm. Strength: Strong; wiry and flexible. Angle: About 45° from stein axis. Texture and luster: Densely pubescent; moderately glossy. Color: Close to 144A.

*Reproductive organs*.—Stamens: Quantity per flower: About five. Filament length: About 1 cm. Filament color: Close to 154D. Anther size: About 0.5 mm by 1 mm. Anther shape: Oblong. Anther color: Close to 9A. Pollen amount: None observed. Pistils: Quantity per flower: One. Pistil length: About 1.25 cm. Style length: About 1.2 cm. Style color: Close to 144B. Stigma diameter: About 0.5 mm. Stigma shape: Tapering. Stigma color: Close to 144B. Ovary color: Close to 144A to 144B.

*Seeds and fruits*.—To date, seed and fruit development has not been observed on plants of the new *Jamesbrittenia*.

Pathogen & pest resistance: Plants of the new *Jamesbrittenia* have been observed to be relatively resistant to *Botrytis cinerea*. To date, plants of the new *Jamesbrittenia* have not been noted to be resistant to pests or other pathogens common to *Jamesbrittenia* plants.

Garden performance: Plants of the new *Jamesbrittenia* have been observed to have excellent garden performance and have been observed to tolerate rain, wind and temperatures ranging from about 1° C. to about 35° C.

It is claimed:

1. A new and distinct *Jamesbrittenia* plant named 'INJAMSADAW' as illustrated and described.

* * * * *